US00PP20921P2

(12) United States Plant Patent
Kleinhanns

(10) Patent No.: US PP20,921 P2
(45) Date of Patent: Apr. 6, 2010

(54) ***SEDUM* PLANT NAMED 'FLORSEBLAB'**

(50) Latin Name: *Sedum spectabile*
Varietal Denomination: Florseblab

(75) Inventor: Christoph E. Kleinhanns, Gernrode (DE)

(73) Assignee: Florensis Hamer CS, Hendrik Ido Ambacht (NL)

( * ) Notice: Subject to any disclaimer, the term of this patent is extended or adjusted under 35 U.S.C. 154(b) by 0 days.

(21) Appl. No.: 12/317,389

(22) Filed: Dec. 22, 2008

(51) Int. Cl.
*A01H 5/00* (2006.01)

(52) U.S. Cl. ..... Plt./479

(58) Field of Classification Search ..... Plt./479
See application file for complete search history.

*Primary Examiner*—Annette H Para
(74) *Attorney, Agent, or Firm*—Jondle & Associates, P.C.

(57) ABSTRACT

A new *Sedum* plant particularly distinguished by having dark brown-black leaves with shiny dark-red flowers, a compact plant habit and high mildew tolerance, is disclosed.

1 Drawing Sheet

Genus and species: *Sedum spectabile* hybrid.
Variety denomination: 'FLORSEBLAB'.

BACKGROUND OF THE NEW PLANT

The present invention comprises a new and distinct cultivar of *Sedum*, botanically known as *Sedum spectabile* hybrid, and hereinafter referred to by the cultivar name 'FLORSEBLAB'. 'FLORSEBLAB' originated from a cross conducted in August 2004 in a cultivated field in Quedlinburg Sachsen-Anhalt Germany. The female parent was a proprietary *Sedum* plant named '1630-04' (unpatented) with light brown leaves and black-red flowers. The male parent was a proprietary *Sedum* plant named '2544-04' (unpatented) with light brown leaves.

The new cultivar was created in August 2004 in Quedlinburg Sachsen-Anhalt Germany, and has been asexually reproduced repeatedly by vegetative cuttings in Quedlinburg Sachsen-Anhalt, Germany over a three-year period. The present invention has been found to retain its distinctive characteristics through successive asexual propagations.

Plant Breeder's Rights for this cultivar have not been applied for. 'FLORSEBLAB' has not been made publicly available more than one year prior to the filing of this application.

SUMMARY OF THE INVENTION

The most outstanding and distinguishing characteristic of this new cultivar when grown under normal horticultural practices in Quedlinburg Sachsen-Anhalt Germany:

a. Dark-brown-black leaves with shiny dark-red flowers;
b. Compact plant habit; and
c. High mildew tolerance.

DESCRIPTION OF THE PHOTOGRAPH

This new *Sedum* plant is illustrated by the accompanying photograph which shows the overall plant; the colors shown are as true as can be reasonably obtained by conventional photographic procedures.

The photograph is of an 18-week old plant grown outside in a greenhouse in Quedlinburg Sachsen-Anhalt, Germany in the spring to summer.

DESCRIPTION OF THE NEW CULTIVAR

The following detailed description sets forth the distinctive characteristics of 'FLORSEBLAB'. The data which define these characteristics were collected from asexual reproductions carried out in Quedlinburg Sachsen-Anhalt, Germany. The plant history was taken on 18-week old plants, in spring and summer and pinched once, two weeks after potting. Rooted cuttings were planted in 12 cm to 15 cm pots and grown in a greenhouse in Quedlinburg Sachsen-Anhalt, Germany. Color readings were taken under natural light. Color references are primarily to the R.H.S. Colour Chart of The Royal Horticultural Society of London (R.H.S.) 1986 edition.

DETAILED BOTANICAL DESCRIPTION

Classification:

*Family.*—Crassulaceae.
*Botanical.*—*Sedum spectabile* hybrid.
*Common name.*—*Sedum.*

Parentage:

*Female parent.*—'1630-04' (unpatented) *Sedum* plant with light brown leaves and black-red flowers.
*Male parent.*—'2544-04' (unpatented) *Sedum* plant with light brown leaves.

Growth:

*Form.*—Upright.
*Height (measured from the top of the soil).*—30 cm.
*Width.*—25 cm.
*Propagation.*—Terminal tips for cutting.
*Time to produce a finished flowering plant.*—10 to 12 weeks.
*Time to initiate and develop roots.*—10 to 14 days.
*Root description.*—White, well-branched, strong.

Leaves:

*Arrangement.*—Opposite.

*Immature leaf.*—Color: Upper surface: RHS 187A Lower surface (general color): Brown-grey Length: 3.0 cm Width: 2.5 cm.
*Mature leaf.*—Color: Upper surface: RHS 187A Lower surface: Brown-grey, similar to RHS 201 Length: 4.0 cm Width: 3.0 cm.
*Apex description.*—Pointed.
*Base description.*—Sitting around stem.
*Shape.*—Ovate.
*Margin.*—Dentate.
*Texture* (*both surfaces*).—Smooth.
*Venation pattern* (*main vein*).—Pinnate.
*Venation color.*—RHS 187A.

Stems:
*Length.*—30 cm.
*Internode length.*—5 cm to 6 cm.
*Color.*—RHS 187C and RHS 187D.
*Texture.*—Smooth.

Flower buds:
*Length.*—0.2 cm.
*Diameter.*—0.2 cm.
*Shape.*—Round.
*Color.*—RHS 186B.

Inflorescence:
*Type.*—An umbel composed of 10 flowers.
*Umbel diameter.*—2 cm to 3 cm.
*Umbel depth* (*height*).—2 cm.
*Umbel shape.*—Flattened globular.
*Flower shape.*—Single, rotate, slightly cup-shaped.
*Flower aspect.*—Upright to slightly outward.
*Blooming habit* (*flowering season*).—Summer to Autumn.
*Lastingness of flowers on the plant.*—4 to 6 weeks.
*Fragrance.*—Absent.
*Peduncle.*—Length: 1 cm to 2 cm Diameter: 0.2 cm Texture: Smooth Color: RHS 191A.
*Pedicel.*—Length: 0.3 cm Diameter: 0.1 cm Texture: Smooth Color: RHS 191A.

Petals:
*Arrangement.*—Star-shaped.
*Number.*—5.
*Length.*—0.3 cm to 0.4 cm.
*Width.*—0.1 cm to 0.2 cm.
*Shape.*—Triangle.
*Apex.*—Acute.
*Base.*—Rounded.
*Margin.*—Entire.
*Texture* (*both surfaces*).—Smooth.
*Color* (*both surfaces*).—RHS 75D.

Sepals:
*Arrangement.*—Campanulate.
*Number.*—5.
*Length.*—0.2 cm to 0.3 cm.
*Width.*—0.2 cm.
*Shape.*—Triangle.
*Apex.*—Acute.
*Texture* (*both surfaces*).—Smooth.
*Color* (*both surfaces*).—RHS 194B.

Reproductive organs:
*Stamen number.*—10 to 12.
*Anther.*—Shape: Irregular round Color (general): Cream Length: 0.1 cm Diameter: 0.1 cm.
*Ovules.*—Shape: Oval Length: 0.1 cm Width: 0.1 cm Texture: Smooth Color (general): Lemon-green.
*Pollen.*—Amount: Sparse Color (general): Cream.
*Pistils.*—Number: 5 Length: 0.2 cm Diameter: 0.2 cm Stigma: Color (general): Rose-pink Shape: V-Shaped Length: 0.3 cm Diameter: 0.2 cm Style: Color: Rose-pink) Length: 0.3 cm Diameter: 0.2 cm Shape: V-shaped.

Fruit and seed set: None observed.

Disease and insect resistance: No special observations made; however 'FLORSEBLAB' has higher mildew tolerance than typical *sedum* cultivars.

COMPARISON WITH PARENTAL AND COMMERCIAL CULTIVARS

'FLORSEBLAB' differs from its female parent, '1630-04' (unpatented) by having dark brown-black leaves and shiny dark-red flowers, while '1630-04' has lighter brown leaves and black-red flowers.

'FLORSEBLAB' differs from its male parent, '2544-04' (unpatented) by having darker brown-black leaves and a higher mildew tolerance than '2544-04'.

'FLORSEBLAB' differs from 'Postman's Pride' (U.S. Plant Pat. No. 16,831) by having a compact plant habit and shiny dark-red flowers, while 'Postman's Pride' has an open plant habit and black-red flowers.

I claim:

1. A new and distinct cultivar of *Sedum* plant as shown and described herein.

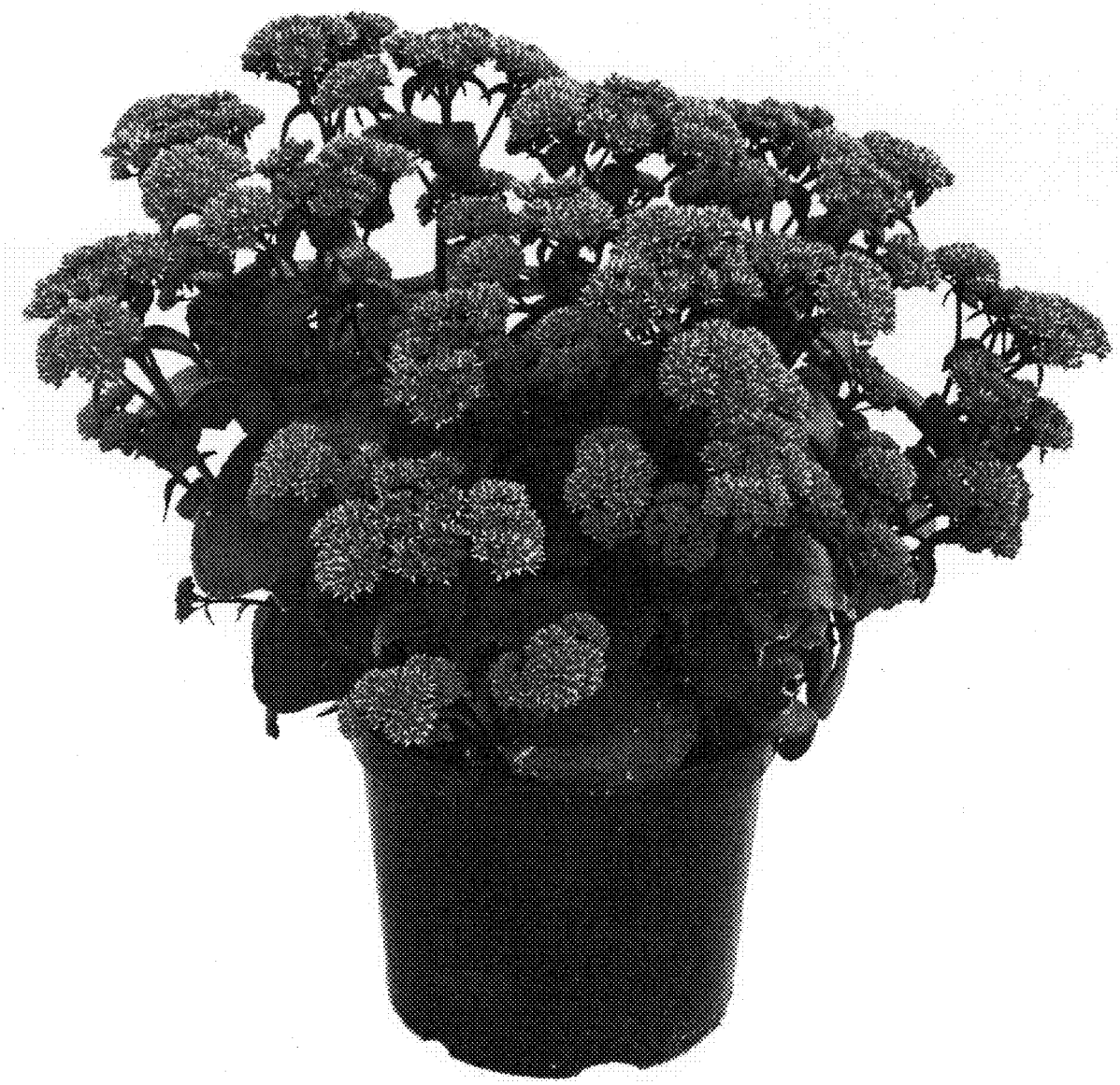

* * * * *